United States Patent [19]

Salman et al.

[11] 4,447,622

[45] May 8, 1984

[54] PREPARATION OF L- AND D-ISOMERS OF DL-3,4-TRANS-2,2-DISUBSTITUTED-3,4-DIARYLCHROMANS AND DERIVATIVES THEREOF

[75] Inventors: Mohammad Salman; Suprabhat Ray; Ved P. Kamboj; Nitya Anand, all of Lucknow, India

[73] Assignee: Council of Scientific and Industrial Research Rafi Marg, New Delhi, India

[21] Appl. No.: 304,507

[22] Filed: Sep. 22, 1981

[51] Int. Cl.$^3$ .................. C07D 405/12; C07D 311/74
[52] U.S. Cl. .................................... 548/525; 544/151; 544/376; 546/196; 549/406
[58] Field of Search ....................... 549/406; 548/525; 546/196; 544/151, 376

[56] References Cited

U.S. PATENT DOCUMENTS 4,251,537  2/1981  Evans ................................. 424/267

OTHER PUBLICATIONS

Eliel, Stereochemistry of Carbon Compounds, McGraw-Hill, New York, (1962), pp. 49 & 50.

*Primary Examiner*—Richard Raymond
*Attorney, Agent, or Firm*—Ladas & Parry

[57] ABSTRACT

The laevo and dextro forms of dl-3,4-trans-2,2-disubstituted-3,4-diarylchromans and similar derivatives thereof have substantially double the post-coital antifertility activity of the known racemic compound. The resolution of such known compound into the l- and d-isomeric forms may be carried out using di-p-toluoyl-l-tartaric acid monohydrate or di-p-toluoyl-d-tartaric acid.

2 Claims, No Drawings

PREPARATION OF L- AND D-ISOMERS OF DL-3,4-TRANS-2,2-DISUBSTITUTED-3,4-DIARYL-CHROMANS AND DERIVATIVES THEREOF

The present invention relates to novel optically active isomers possessing improved potency as post-coital anti-fertility agents for females. More particularly, the invention relates to novel optically active l- and d-isomers of dl-3,4-trans-2,2-disubstituted-3,4-diarylchromans and derivatives thereof, a process for their preparation and pharmaceutical compositions containing such isomers as active ingredient.

With the importance that governments attach nowadays to family planning, it is not difficult to appreciate that considerable research has been effected in the past and continues to be effected for the development of better, more effective agents for the control and planning of birth. Chemical anti-fertility agents for oral use can be of two types, either anti-coital or post-coital agents. It is with the latter type of agents in so far as they are applicable to females that the present invention relates.

Among hitherto known post-coital anti-fertility agents dl-3,4-trans-3-phenyl-4-[p-($\beta$-pyrrolidinoethoxy)]phenyl-7-methoxychroman has acquired a reputation. The compound in question forms the subject of U.S. patent application Ser. No. 260,849 of J. W. Bolger filed on the 8th June 1972 and of the corresponding German and French patents which were applied for in 1973. Furthermore, applicants' Indian Pat. No. 129187 dated the 12th November 1970 describes one process for the preparation of dl-3,4-trans-3-phenyl-4-[p-($\beta$-pyrrolidinoethoxy)]phenyl-7-methoxychroman and its related compounds. This procedure was subsequently published in J. Med. Chem. 19(2), 276–279 (1976) by Ray et al.

According to Indian Pat. No. 129187, the process for the production of dl-3,4-trans-3-phenyl-4-[p-($\beta$-pyrrolidinoethoxy)]phenyl-7-methoxychroman comprises reacting a compound of the general formula:

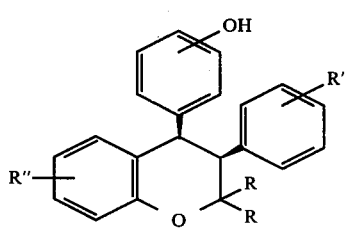

wherein R is lower alkyl, R' and R" can be hydroxy, chloro, fluro, trifluoromethyl, lower alkyl, lower alkoxy or tertiary amino lower alkoxy groups with $\beta$-chloroethyl pyrrolidine in a ketonic solvent in the presence of an acid binding agent to obtain the compound of the formula:

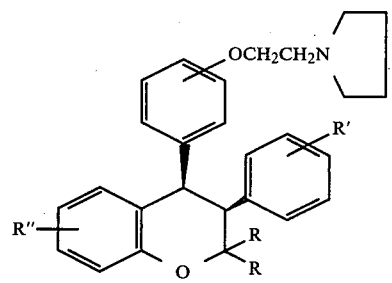

wherein R, R' and R" have the meanings stated above, and if desired, isomerising the obtained compound with a strong base in a raprotic solvent to a compound of the formula:

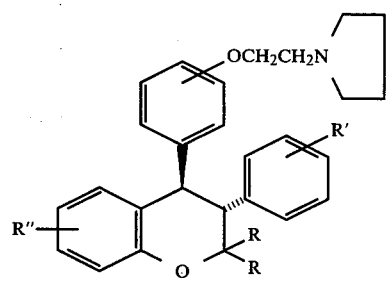

wherein R, R' and R" have the meanings stated above.

Proceeding with the Indian Pat. No. 129187 as basis, the applicants have effected additional research which has revealed most encouraging results. The anti-fertility activity of dl-3,4-trans-2,2-dimethyl-3-phenyl-4-[p-($\beta$-pyrrolidinoethoxy)]phenyl-7-methoxychroman was known. Accordingly, the fact that an alternative isomeric form of this compound should display twice as much potency as a post-coital anti-fertility agent in females is both unexpected and advantageous. The applicants discovered that by the resolution of the known racemic compound to the optically active laevo (l) or dextro (d) isomeric forms, they achieved compounds which evince, particularly in the case of the l-isomeric form, substantially double the activity as a post-coital anti-fertility agent over the known dl-isomer.

The present invention therefore provides as new compounds laevo and dextro forms of dl-3,4-trans-2,2-disubstituted-3,4-diarylchromans, specifically l-3,4-trans-2,2-dimethyl-3-phenyl-4-[p-($\beta$-pyrrolidinoethoxy)]phenyl-7-methoxychroman and d-3,4-trans-2,2-dimethyl-3-phenyl-4-[p-($\beta$-pyrrolidinoethoxy)]phenyl-7-methoxychroman.

The new compounds correspond to the general formula:

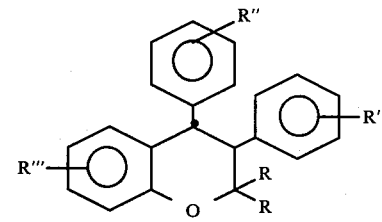

wherein R is lower alkyl and each of R', R" and R'"
may be hydroxy, chloro, fluro, trifluoromethyl, lower
alkyl or tertiary amino lower alkoxy.

The invention includes within its scope the optically
active l-acid and d-acid salts of the new compounds
referred to above. These salts are characterised by the
general formula:

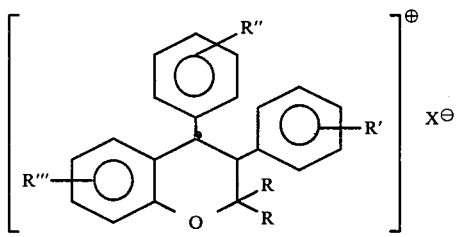

wherein X denotes the optically active anion and R, R',
R" and R'" have the meanings stated above.

As employed herein, the expressions "lower alkyl"
and "lower alkoxy" embrace both straight and
branched chain alkyl and alkoxy radicals, respectively,
containing from 1 to 6 carbon atoms. Thus, for example,
"lower alkyl" includes methyl, ethyl, n-propyl, isopropyl, n-butyl, tert-butyl, n-amyl, sec-amyl, n-hexyl, 2-ethybutyl and 2,3-dimethylbutyl while "lower alkoxy"
includes methoxy, ethoxy, n-propoxy, isopropoxy, n-butyoxy, tert-butoxy, n-amyloxy, sec-amyloxy n-hexyloxy, 2-ethyl-butyoxy and 2,3-dimethylbutoxy.

The tertiary amino radical consists of dialkylamines
such as dimethyl, diethyl, dipropyl, dibutyl, or polymethyleneimines such as piperidine, pyrrolidine, N-methyl
piperazine and morpholine.

Preferably R is lower alkyl, R' is hydrogen, R" is in
the 4-position and is tertiary amino-lower alkoxy such
as pyrrolidino-lower alkoxy, and R'" is in the 7-position
and is lower alkoxy.

According to a preferred feature, the present invention provides a process for the preparation of optically
active l- and d-isomers of dl-3,4-trans-2,2-disubstituted-3,4-diarylchromans and optically active acid salts
thereof which comprises reacting a dl-3,4-trans-2,2-disubstituted-3,4-diarylchroman compound of the general formula:

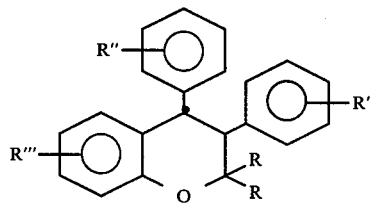

wherein R is lower alkyl and each of R', R", R'" may be
a hydroxy, chloro, fluoro, trifluoromethyl, lower alkyl,
or tertiary amino lower alkoxy group with an optically
active acid in a protic solvent to produce an optically
active acid salt of the formula:

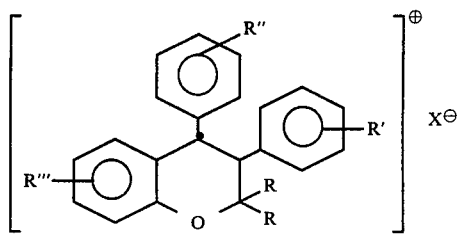

wherein X denotes the optically active acid anion, subjecting the reaction mixture to fractional crystallisation
to obtain said salt in crystalline form and subjecting the
crystalline salt to aklaine hydrolysis to obtain the desired isomer.

According to a further feature, the invention provides a process for the preparation of 1-3,4-trans-2,2-dimethyl-3-phenyl-4-[p-(β-pyrrolidinoethoxy)]phenyl-7-methoxychroman of the general formula:

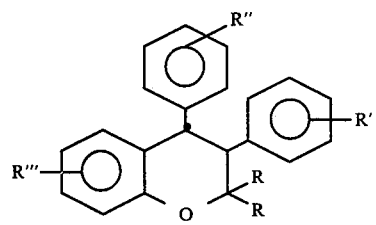

wherein R, R', R", R'" have the meanings stated herein
and optically active l-acid salts thereof, which comprises reacting dl-3,4-trans-2,2-dimethyl-3-phenyl-4-[p-(β-pyrrolidinoethoxy)]phenyl-7-methoxychroman of
the general formula:

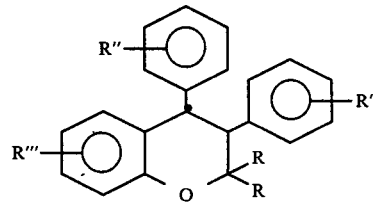

wherein R, R', R", and R'" have the meanings stated
above with an optically active l-acid in a protic solvent
to produce on fractional crystallisation of the reaction
mixture an 1-3,4-trans-2,2-dimethyl-3-phenyl-4-[p-(β-pyrrolidinoethoxy)]phenyl-7-methoxychroman-l-acid
salt of the general formula:

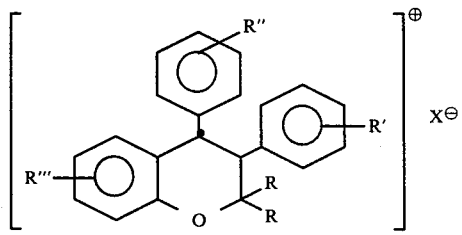

wherein X denotes the optically active anion and R, R',
R" and R'" have the meanings stated above and subjecting said crystalline salt to alkaline hydrolysis to obtain the desired l-isomer.

According to a still further feature, the invention provides a process for the preparation of d-3,4-trans-2,2-dimethyl-3-phenyl-4-[p-(β-pyrrolidinoethoxy)]phenyl-7-methoxychroman of the general formula:

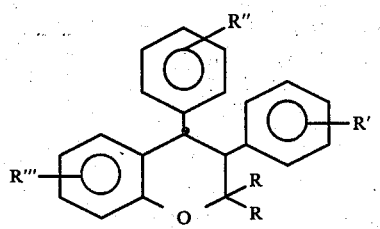

wherein R, R', R" and R'" have the meanings stated herein and optically active d-acid salts thereof which comprises reacting dl-3,4-trans-2,2-dimethyl-3-phenyl-4-[p-(β-pyrrolidinoethoxy)]phenyl-7-methoxychroman of the general formula:

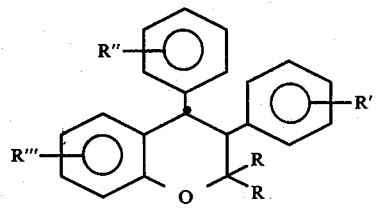

wherein R, R', R" and R'" have the meanings stated above with an optically active d-acid in a protic solvent to produce on fractional crystallisation of the reaction mixture a d-3,4-trans-2,2-dimethyl-3-phenyl-4-[p-(β-pyrrolidinoethoxy)]phenyl-7-methoxychroman-d-acid salt of the general formula:

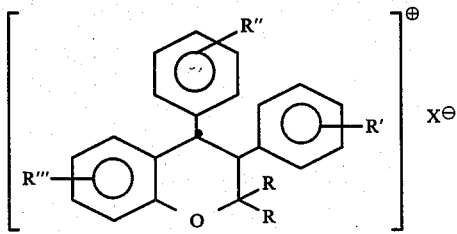

wherein X denotes the optically active anion and R, R', R" and R'" have the meanings stated above and subjecting said crystalline salt to alkaline hydrolysis to obtain the desired d-isomer.

The preferred optically active l-acid is di-p-toluoyl-l-tartaric acid monohydride while the preferred optically active d-acid is di-p-toluoyl-d-tartaric acid.

Examples of the protic solvents which may be employed in the reaction include methanol, benzene or a mixture of the two.

According to yet another embodiment, the invention provides a post-coital anti-fertility composition comprising as active ingredient an optically active l-isomer of a dl-3,4-trans-2,2-disubstituted-3,4-diarylchroman or an optically active acid derivative thereof in combination with a pharmaceutically acceptable carrier or excipient therefor.

Examples of the carriers or excipients with which the active ingredient may be combined to provide the above-mentioned composition include starch, dicalcium phosphate and calcium stearate and combinations of any of these.

The efficacy of the novel 1-3,4-trans-2,2-dimethyl-3-phenyl-4-[p-(β-pyrrolidinoethoxy)]phenyl-7-methoxychroman was proved on female albino rats and was found to possess twice the anti-fertility activity of the known dl-compound. Adult female albino rats were treated by the oral route with the active compound of the invention for a period of from 1 to 5 days in a post-coital schedule. The dosage employed was 0.125 mg/kg or higher and was found effectively to prevent pregnancy. Details of the experiments carried out are set out in the Table shown hereunder:

TABLE

Antifertility Efficacy of Laevo-centchroman in Female Albino Rats

| Dose (mg/kg/day) | Oral Feeding on days post-coitum | Number of rats taken | Number pregnant | % Anti-fertility efficacy |
|---|---|---|---|---|
| 0.50 | 1–7 | 6 | 0 | 100 |
| 0.20 | 1–7 | 6 | 0 | 100 |
| 0.125 | 1–7 | 10 | 0 | 100 |
| 0.10 | 1–7 | 100  0 | 100 | |
| 0.05 | 1–7 | 10 | 2(7,2)* | 80 |

*Number of implants in each pregnant animal.

The preparation of the novel compounds and its derivatives are described in greater detail in the following non-limitative Examples.

EXAMPLE I 1-3,4-trans-2,2-dimethyl-3-phenyl-4-[p-(β-pyrrolidinoethoxy)]phenyl-7-methoxychroman-di-p-toluoyl-l-tartrate dl-3,4-trans-2,2-dimethyl-3-phenyl-4-[p-(β-pyrrolidinoethoxy)]phenyl-7-methoxychroman and di-p-toluoyl-l-tartaric acid monohydrate in 1:0.5 equivalent molar ratio were taken in absolute methanol and stirred for 2 hours. Methanol was evaporated off and the residual oil was crystallized from a benzene-methanol mixture to give 1-3,4-trans-2,2-dimethyl-3-phenyl-4-[p-(β-pyrrolidinoethoxy)]phenyl-7-methoxychroman-di-p-toluoyl-l-tartrate, m.p. 120°[α]$_D^{20}$−117.2° (c 0.93 in CHCl$_3$).

EXAMPLE II 1-3,4-trans-2,2-dimethyl-3-phenyl-4-[p-(β-pyrrolidinoethoxy)]phenyl-7-methoxychroman The 1-3,4-trans-2,2-dimethyl-3-phenyl-4-[p-(β-pyrrolidinoethoxy)]phenyl-7-methoxychroman-di-p-toluoyl-l-tartrate salt obtained from Example I was hydrolysed by taking it in chloroform and treating it with aqueous alkali. The organic layer was washed with water to neutral, dried over anhydrous sodium sulphate and concentrated to yield colourless crystalline 1-3,4-trans-2,2-dimethyl-3-phenyl-4-[p-(β-pyrrolidinoethoxy)]phenyl-7-methoxychroman. [α]$_D^{20}$− 192.9° (c 0.57 in CHCl$_3$), m.p. (as hydrochloride salt) 197°.

EXAMPLE III d-3,4-trans-2,2-dimethyl-3-phenyl-4-[p-(β-pyrrolidinoethoxy)]phenyl-7-methoxychroman-di-p-toluoyl-d-tartrate.

dl-3,4-trans-2,2-dimethyl-3-phenyl-4-[p-(β-pyrrolidinoethoxy)]phenyl-7-methoxychroman and di-p-toluoyl-d-tartaric acid in 1:0.5 equivalent molar ratio were taken in absolute methanol and stirred for 2 hours. Methanol was then evaporated off and the residual oil was crystallized from a benzene-methanol mixture to give d-3,4-trans-2,2-dimethyl-3-phenyl-4-[p-(β-pyrrolidinoethoxy)]phenyl-7-methoxychroman-di-p-toluoyl-d-tartrate as a colourless crystalline solid. m.p. 138°, $[\alpha]_D^{20}$, +117.2° (c 1.0 in CHCl$_3$).

EXAMPLE IV d-3,4-trans-2,2-dimethyl-3-phenyl-4-[p-(β-pyrrolidinoethoxy)]phenyl-7-methoxychroman.

The d-3,4-trans-2,2-dimethyl-3-phenyl-4-[p-(β-pyrrolidinoethoxy)]phenyl-7-methoxychroman-di-p-toluoyl-d-tartrate salt obtained from Example III was hydrolysed by taking it in chloroform and treating it with aqueous alkali. The organic layer was washed with water to neutral, dried over anhydrous sodium sulphate and concentrated to yield colourless crystalline d-3,4-trans-2,2-dimethyl-3-phenyl-4-[p-(β-pyrrolidinoethoxy)]phenyl-7-methoxychroman$[\alpha]_D^{20}$+192.9° (c 1.0 in CHCl$_3$). m.p. (as hydrochloride salt) 197°.

We claim:

1. A process for the preparation of l-3,4-trans-2,2-dimethyl-3-phenyl-4-[p-(β-pyrrolidinoethoxy)]phenyl-7-methoxychroman or active l-acid salts thereof, which comprises reacting dl-3,4-trans-2,2-dimethyl-3-phenyl-4-[p-(β-pyrrolidinoethoxy)]phenyl-7-methoxy chroman with di-p-toluoyl-l-tartaric acid monohydrate in a protic solvent to produce on fractional crystallisation of the reaction mixture the l-3,4-trans-2,2-dimethyl-3-phenyl-4-[p-(β-pyrrolidino-ethoxy)]phenyl-7-methoxy chroman-l-acid salt of said tartaric acid monohydrate and subjecting said crystalline salt to alkaline hydrolysis to obtain the desired l-isomer.

2. A process as claimed in claim 1, wherein the protic solvent is methanol, benzene or a mixture of methanol and benzene.

* * * * *